United States Patent [19]
Hill

[11] Patent Number: 5,163,195
[45] Date of Patent: Nov. 17, 1992

[54] CONVERTIBLE HEAD IMMOBILIZER PILLOW

[76] Inventor: John S. Hill, 440 E. Juanita Ave., Gilbert, Ariz. 85234

[21] Appl. No.: 792,463

[22] Filed: Nov. 12, 1991

[51] Int. Cl.$^5$ ............................................. A47G 9/00
[52] U.S. Cl. ......................................... 5/637; 5/640; 5/648; 5/922
[58] Field of Search ................. 5/637, 640, 648, 465, 5/636, 922

[56] References Cited

U.S. PATENT DOCUMENTS

| | | | |
|---|---|---|---|
| 1,153,120 | 9/1915 | Lackey | 5/465 |
| 2,589,579 | 3/1952 | Slayen | 5/465 |
| 4,163,297 | 8/1979 | Neumark | 5/465 |
| 4,924,543 | 5/1990 | Hoss et al. | 5/484 |

*Primary Examiner*—Alexander Grosz
*Attorney, Agent, or Firm*—Jordan M. Meschkow; Don J. Flickinger; Lowell W. Gresham

[57] ABSTRACT

A convertible pillow having two head rolls coupled by a headrest in a spaced-apart relationship, each having a support member coupled thereto allowing for conversion into a variety of configurations. Attachment members are coupled to the head rolls and the support members for holding convertible pillow in a pillow configuration, and in a head immobilizing configuration. The convertible pillow is securely attached to a mattress by placing a mattress sock over the end of the mattress and attaching the convertible pillow to the mattress sock by the attachment members.

8 Claims, 2 Drawing Sheets

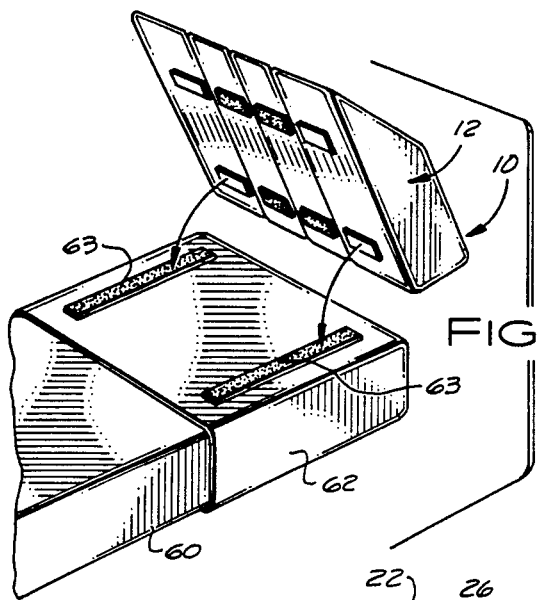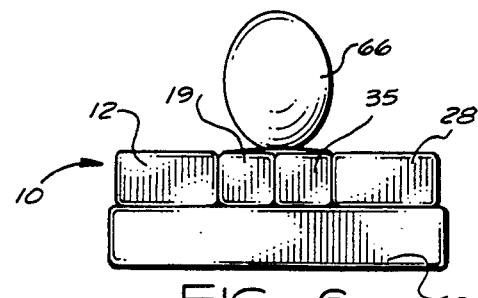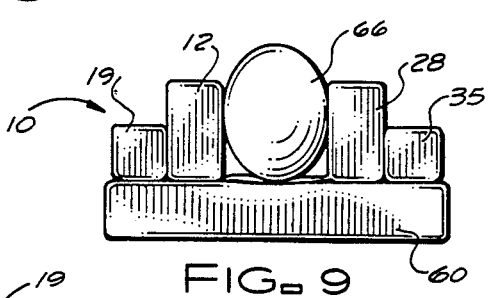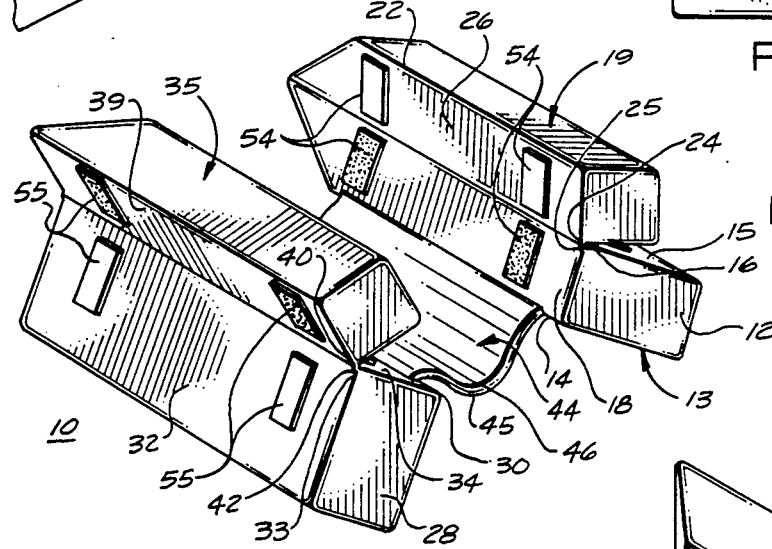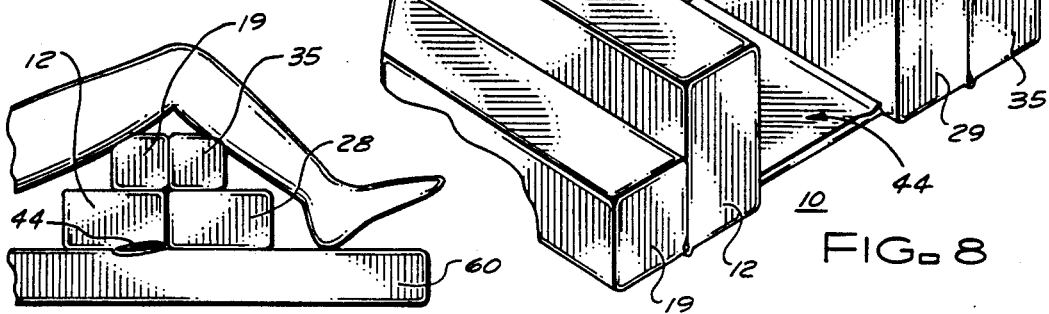

CONVERTIBLE HEAD IMMOBILIZER PILLOW

BACKGROUND OF THE INVENTION

1. Field of the Invention

The present invention relates to head and neck support and immobilization devices.

More particularly, the present invention relates to a pillow for use on an ambulance gurney, which is convertible to lateral head rolls for supporting a human head.

2. Prior Art

When patients are transferred from accident sites to hospitals, ambulances or helicopters are usually used. The patient is first placed on a rolling bed or gurney, which is then placed in the emergency vehicle. Generally, a gurney includes a mattress upon which the patient lies, and a pillow to support the patient's head. Ambulances typically use ordinary pillows for their gurneys, which have a number of disadvantages. These pillows are usually of a standard size having no means for adjustment to different sized patients. These pillows also lie loosely upon the gurney mattress, which allows them to be lost or dropped during transfer of the patient or when bringing the gurney to a patient. The largest drawback of the standard pillow, is that they provide no head support for patient's who have neck or spinal injuries.

A great many patients being transferred to hospitals have known or possible neck injuries, especially those involved in an automobile accident. In these cases, special precautions need to be observed in the movement of a person after the injury. The head of these patients must be immobilized to prevent further injury or to prevent aggravation of existing injuries. Traditional methods of immobilizing the head and neck of a patient usually involve placing a cervical collar around the neck, placing sandbags along the head and neck, and securely strapping the head to a rigid backboard. Many times a patient is placed on a backboard and opposing head support pads are placed on opposite sides of the patient's head. These pads and the patient's head are then securely fastened to the rigid board. In these cases, the board is then placed on the gurney and the gurney is placed in the emergency vehicle. The standard pillow is of no use and is simply in the way.

When there is no neck or head injury, and the gurney alone is used, the pillow supports the patient's head. However, a pillow should be used only once for sanitary reasons, before it is disposed of. The pillow is also easily lost or left at a hospital when the patient is removed. Further, when there is a neck injury, the pillow becomes an unnecessary object which is in the way. Emergency vehicles require storage space for head rolls as well as pillows to provide the necessary head support for different situations.

It would be highly advantageous, therefore, to remedy the foregoing and other deficiencies inherent in the prior art.

Accordingly, it is an object of the present invention to provide an improved gurney pillow.

Another object of the present invention is to provide an adjustable pillow for use with gurneys.

And another object of the present invention is to provide a pillow which can be convertible into a head immobilizer.

Still another object of the present invention is to provide a pillow which will not fall off a gurney.

And still another object of the present invention is to provide a head immobilizer which is easily adjustable to any size head and is simple to use.

Yet another object of the present invention is to provide a convertible head immobilizer pillow which is easily sanitized.

Yet still another object of the present invention is to provide a convertible head immobilizer pillow which can be compactly folded for easy storage.

SUMMARY OF THE INVENTION

Briefly, to achieve the desired objects of the invention in accordance with the preferred embodiment thereof, provided are first and second head rolls, each defined by an upper surface having an edge and a lower surface having an edge. A headrest is joined to the upper edge of the first head roll and the upper edge of the second head roll, coupling said first and second head rolls in a spaced apart relationship. Also provided, are first and second support members, each defined by an upper surface having an edge and a lower surface having an edge. The lower edge of the first support member is coupled to the lower edge of the first head roll by a seam, and the lower edge of the second support member is hingedly coupled to the lower edge of the second head roll by a seam. Attachment members are coupled to the lower surfaces and vertical surfaces of the first and second head rolls and the first and second support members.

The present invention has two major positions, a first position forming a pillow structure having a beveled edge, and a second position forming a head immobilizer structure.

BRIEF DESCRIPTION OF THE DRAWINGS

The foregoing and further and more specific objects and advantages of the instant invention will become readily apparent to those skilled in the art from the following detailed description of the preferred embodiment thereof taken in conjunction with the drawings in which:

FIG. 5 is a perspective view of the present invention in pillow configuration illustrating its installation on a gurney mattress;

FIG. 6 is an end view of the present invention in pillow configuration;

FIG. 7 is a perspective view of the present invention illustrating its convertibility to a head immobilizing configuration;

FIG. 8 is a perspective view of the present invention in its head immobilizer configuration;

FIG. 9 is an end view of the present invention in its head immobilizer configuration; and FIG. 10 is a side view of the present invention being used as a support device.

DESCRIPTION OF THE PREFERRED EMBODIMENT

Figure 3:
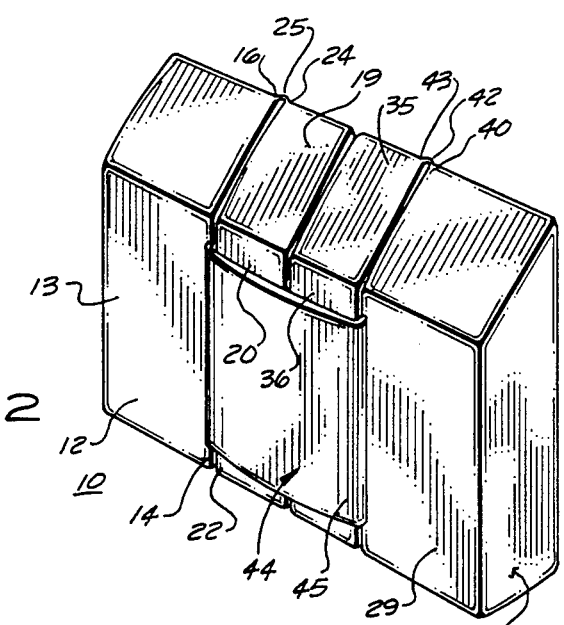
FIG. 3 is a perspective view of the present invention in its pillow configuration.
Figure 4:
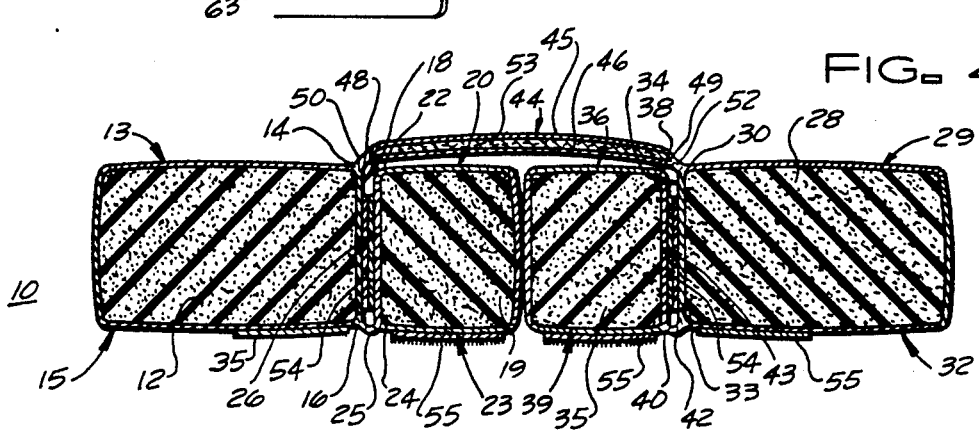
FIG. 4 is a cross-sectional view of the present invention taken along line 4 of FIG. 2.

Turning now to the drawings in which like reference characters indicate corresponding elements throughout the several views, attention is first directed to FIGS. 3 and 4, which illustrate a convertible head immobilizing pillow generally designated 10. Pillow 10 has a first head roll 12 defined by an upper surface 13 having an upper edge 14 and a lower surface 15 having a lower edge 16. A vertical surface 18 extends between upper edge 14 and lower edge 16, joining upper surface 13 and lower surface 15 in a spaced apart relationship. A first support member 19 defined by an upper surface 20 having an upper edge 22, and a lower surface 23 having a lower edge 24, is hingedly coupled to first head roll 12 by a seam 25 which joins lower edge 16 of first head roll 12 to lower edge 24 of first support member 19. Upper surface 20 and lower surface 23 of first support member 19 are coupled in a spaced apart relationship by a vertical surface 26 extending between upper edge 22 and lower edge 24.

Convertible pillow 10 has a second head roll 28 defined by an upper surface 29 having an upper edge 30, and a lower surface 32 having a lower edge 33. A vertical surface 34 extends between upper edge 30 and lower edge 33, coupling upper surface 29 and lower surface 32 in a spaced apart relationship. A second support member 35 defined by an upper surface 36 having an upper edge 38 and a lower surface 39 having a lower edge 40, is hingedly coupled to second head roll 28 by a seam 42 joining lower edge 40 of second support member 35 to lower edge 33 of second head roll 28. A vertical surface 43 extends between upper edge 38 and lower edge 40 of support member 35, coupling upper surface 36 and lower surface 39 in a spaced apart relationship.

A headrest 44 consists of an upper layer 45 and a lower layer 46 joined at their periphery, and having an edge 48 and an edge 49. Headrest 44 couples first head roll 12 and second head roll 28 in a spaced-apart relationship. Edge 48 of headrest 44 is hingedly coupled to upper edge 14 of first head roll 12 by a seam 50, and edge 49 of headrest 44 is hingedly coupled to upper edge 30 of second head roll 28 by a seam 52. Headrest 44 contains batting 53 between upper layer 45 and lower layer 46. Those skilled in the art will understand that while headrest 44 acts to join first head roll 12 to second head roll 28, and no batting is necessary, the presence of a small amount of batting 53, which may be any material used for this purpose, will provide padding and comfort to a patient.

Turning now to FIG. 7, convertible pillow 10 is illustrated between conversions to one of its configurations. These conversions are possible due to the flexibility of seams 25, 42, 50, and 52. This flexibility allows convertible pillow 10 to be converted into a variety of configurations, two of which are the major configurations. The first major configuration, is the pillow configuration illustrated in FIG. 3, FIG. 4 and FIG. 6. In this configuration, first and second support members 19 and 35, respectively, are placed between first head roll 12 and second head roll 28. In this position, vertical surface 26 of first support member 19 is placed flush with vertical surface 18 of first head roll 12. Vertical surface 43 of second support member 35 is placed flush with vertical surface 44 of second head roll 28. Headrest 44 extends across upper surface 20 of first support member 19 and upper surface 36 of second support member 35. Attachment members 54 consisting of engagement pairs are coupled to vertical surfaces 18, 26, 34 and 43 of first head roll 12 for support member 19, second head roll 28 and second support member 35, respectively. A complemental element of engagement pairs on vertical surface 18 of first head roll 12 fastens to corresponding complemental element on vertical surface 26 of first support member 19, and vertical surface 34 of second head roll 28 fastens to vertical surface 43 of second support member 35, when convertible pillow 10 is in the pillow configuration. Attachment members 54 in this configuration help maintain convertible pillow 10 in its pillow configuration.

A second major configuration of convertible pillow 10 is a head immobilizer configuration illustrated in FIGS. 8 and 9. In this configuration, first head roll 12 and second head roll 28 are tilted so that vertical surfaces 18 and 34 become the bottom. First support member 19 and second support member 35 swing to the outside of first head roll 12 and second head roll 28 so that headrest 44 alone separates first head roll 12 and second head roll 28. Lower surface 23 of first support member 19 becomes vertical, and is placed flush against lower surface 15 of first head roll 12 which also is vertical. Lower surface 39 of second support member 35 becomes vertical and is placed flush against lower surface 32 of second head roll 28 which also becomes vertical. Referring back to FIG. 7, it can be seen that attachment members 55 consisting of engaging pairs of complemental elements are coupled to lower surfaces 15, 23, 32 and 39 of first head roll 12, first support member 19, second head roll 28, and second support member 35, respectively. Attachment members 55 are positioned so that first head roll 12 and first support member 19 are securely fastened to one another and second head roll 28 and second support member 35 are securely fastened to one another, when convertible pillow 10 is in the head immobilizer configuration. Attachment members 54 and 55 are illustrated as the loop and hook fasteners commercially available under the name Velcro TM.

Referring to FIG. 9, a patient's head 66 is placed on headrest 44 between first head roll 12 and second head roll 28. This positioning of head 66 prevents any lateral movement or head turning. Those skilled in the art will understand that while some head immobilization will result when pillow 10 is used in this configuration with a mattress 60, to provide more comprehensive immobilization, a rigid board, not illustrated, would be placed between pillow 10 and mattress 60. When a rigid board is used, batting 53 in headrest 44 will provide some padding, providing the patient more comfort.

Referring now to FIG. 5, a mattress 60 is illustrated over one end of which a mattress sock is placed. Mattress sock 62 fits over an end of mattress 60, completely encircling it. Attachment members 63 are fastened to a top surface 64 of mattress 60. Attachment members 63 are configured to engage attachment members 55 when convertible pillow 10 is in the pillow configuration as illustrated in FIG. 5. Not illustrated is the fastening of attachment members 54 to attachment members 63 of mattress sock 62 when convertible pillow 10 is in the head immobilizer configuration. Since mattress sock 62 is securely fastened to mattress 60, the fastening of convertible pillow 10 to mattress sock 62 prevents it from becoming lost or falling off mattress 60. Therefore, it will always be present when it is needed.

Figure 1:
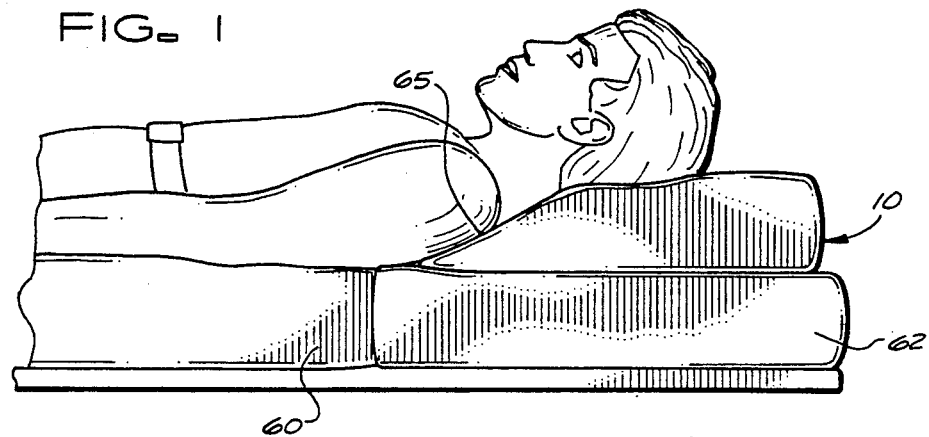
FIG. 1 is a perspective view of a convertible pillow, constructed in accordance with the teachings of the instant invention, as it would appear installed on a gurney mattress in its pillow configuration.

Referring to FIG. 1, the attachment of convertible pillow 10 to mattress sock 62 permits a degree of adjustability for different size patients. As illustrated in FIG. 1, convertible pillow 10 in the pillow configuration can be moved forward or backward on mattress 60, depending on the size of the patient and will be held in place by fastening attachment members 63 to attachment members 55. A beveled edge 65 of convertible pillow 10 in its pillow configuration gives neck support and in conjunction with attachment members 63 and 55, gives an adjustable amount of head support.

Figure 2:
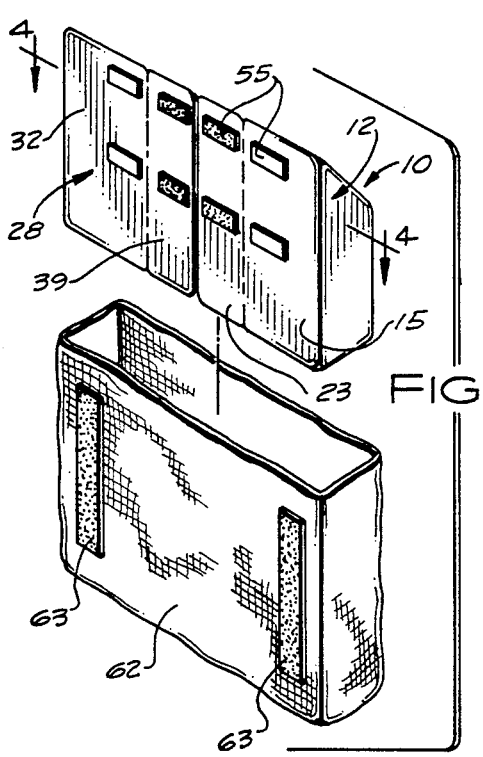
FIG. 2 is a perspective view of a convertible pillow, constructed in accordance with the teachings of the instant invention as it would appear in its pillow configuration and stored in a gurney sock.

FIG. 2 illustrates convertible pillow 10 in its pillow configuration, and mattress sock 62. When not in use, convertible pillow 10 may be placed inside mattress sock 62 and stored in a suitable location. This allows convertible pillow 10 to be present for convenient use, but neatly packaged for easy storage.

Referring now to FIG. 10, convertible pillow 1?, due to its highly foldable nature, can be converted into lesser configurations such as the support structure illustrated in FIG. 10. In this configuration, convertible pillow 10 forms a convenient, padded support structure for use in propping up a patient's leg when injured, and propping up both legs at the feet for treatment of shock. It will be understood by those skilled in the art that there are a variety of other uses to which the convertible pillow in its pillow configuration, its head immobilizing configuration or its support configuration can be used.

Convertible pillow 10, in this preferred embodiment, is constructed with a waterproof fabric that is designed to be sprayed with a disinfectant and wiped clean after every use. This provides a safe environment for subsequent patients without the need for disposing of a stained or infected pillow.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A convertible head immobilizing pillow comprising:
   a first head roll defined by an upper surface having an edge and a lower surface having an edge;
   a headrest hingedly coupled to said upper edge of said first head roll by a seam;
   a first support member defined by an upper surface having an edge and a lower surface having an edge;
   a seam hingedly coupling said lower edge of said first support member to said lower edge of said first head roll;
   a second head roll defined by an upper surface having an edge and a lower surface having an edge;
   a seam hingedly coupling said upper edge of said second head roll to said headrest, opposite said first head roll;
   a second support member defined by an upper surface having an edge and a lower surface having an edge;
   a seam hingedly coupling said lower edge of said second support member to said lower edge of said second head roll.

2. A device as claimed in claim 1 further comprising:
   a mattress sock having attachment members coupled to an upper surface thereof;
   attachment members coupled to said lower surfaces of said first head roll, said first support member, said second head roll, and said second support member.

3. A convertible pillow for use in combination with a mattress comprising:
   a mattress sock configured to receive said mattress;
   a first head roll;
   a second head roll;
   a headrest coupling said first head roll to said second head roll in a spaced-apart relationship;
   a first support member coupled to said first head roll;
   second support member coupled to said second head roll;
   attachment members coupled to said first headrest, said first support said second headrest, and said second support member;
   sock attachment members coupled to said mattress sock, configured to engage said attachment members coupled to said first headrest, said first support member, said second headrest, and said second support member.

4. A convertible pillow as claimed in claim 3 further comprising:
   said first head roll defined by an upper surface having an edge and a lower surface having an edge, coupled by a vertical surface therebetween;
   said headrest hingedly coupled to said upper edge of said first head roll by a seam;
   said first support member defined by an upper surface having an edge and a lower surface having an edge, coupled by a vertical surface therebetween;
   a seam hingedly coupling said lower edge of said first support member to said lower edge of said first head roll;
   said second head roll defined by an upper surface having an edge and a lower surface having an edge, coupled by a vertical surface therebetween;
   a seam hingedly coupling said upper edge of said second head roll to said headrest, opposite said first head roll;
   said second support member defined by an upper surface having an edge and a lower surface having an edge, coupled by a vertical surface therebetween;
   a seam hingedly coupling said lower edge of said second support member to said lower edge of said second head roll.

5. A convertible pillow as claimed in claim 4 which can be converted into a plurality of separate configurations.

6. A convertible pillow as claimed in claim 5 wherein said plurality of separate configurations includes a pillow configuration, and a head immobilizer configuration.

7. A convertible pillow as claimed in claim 6 wherein said pillow configuration comprises:
   said vertical surface of said first support member coupled flush with said vertical surface of said first head roll by said attachment means coupled to said vertical surfaces;
   said vertical surface of said second support member coupled flush with said vertical surface of said second head roll by said attachment means coupled to said vertical surfaces;

said headrest extending between said first head roll and said second head roll over said upper surfaces of said first support member and said second support member;
a beveled surface formed on one end of said convertible pillow when in the pillow configuration.

8. A convertible pillow as claimed in claim 6 wherein said head immobilizer configuration comprises:
said lower surface of said first support member coupled flush with said lower surface of said first head roll by said attachment means coupled to said lower surfaces;
said lower surface of said second support member coupled flush with said lower surface of said second head roll by said attachment means coupled to said lower surfaces;
said headrest coupling said first head roll and said second head roll in a spaced-apart relationship;
said second attachment member configured to engage said sock attachment members.

* * * * *